US010322215B2

United States Patent
Stojcevic et al.

(10) Patent No.: US 10,322,215 B2
(45) Date of Patent: Jun. 18, 2019

(54) FUNCTIONALIZED COPOLYMERS OF ISOOLEFINS AND DIOLEFINS AND THEIR USE AS COMPATIBILIZERS

(75) Inventors: Goran Stojcevic, Antwerp (BE); Gilles Arsenault, London (CA); Elizabeth R. Gillies, London (CA); Collin V. Bonduelle, London (CA); Matthew J. McEachran, Sarnia (CA)

(73) Assignees: LANXESS INTERNATIONAL SA, Granges-Paccot (CH); UNIVERSITY OF WESTERN ONTARIO, London (CA)

(*) Notice: Subject to any disclaimer, the term of this patent is extended or adjusted under 35 U.S.C. 154(b) by 1443 days.

(21) Appl. No.: 13/816,299

(22) PCT Filed: Aug. 11, 2011

(86) PCT No.: PCT/CA2011/050488
§ 371 (c)(1),
(2), (4) Date: Sep. 20, 2013

(87) PCT Pub. No.: WO2012/019303
PCT Pub. Date: Feb. 16, 2012

(65) Prior Publication Data
US 2014/0004252 A1    Jan. 2, 2014

Related U.S. Application Data

(60) Provisional application No. 61/373,358, filed on Aug. 13, 2010.

(51) Int. Cl.
*A61L 31/10* (2006.01)
*A61L 29/08* (2006.01)
(Continued)

(52) U.S. Cl.
CPC .............. *A61L 31/10* (2013.01); *A61L 29/085* (2013.01); *A61L 29/14* (2013.01); *B05D 5/04* (2013.01);
(Continued)

(58) Field of Classification Search
None
See application file for complete search history.

(56) References Cited

U.S. PATENT DOCUMENTS 4,026,967 A    5/1977  Flexman, Jr. et al.
4,444,817 A    4/1984  Subramanian
(Continued)

FOREIGN PATENT DOCUMENTS

WO    9415973 A2    7/1994

OTHER PUBLICATIONS

Ikeda et al. "Chemical Modification of Butyl Rubber. II. Structure and Properties of Poly(ethylene oxide)-Grafted Butyl Rubber" Journal of Polymer Science: Part B: Polymer Physics, vol. 33, 387-394 (1995).*
(Continued)

*Primary Examiner* — Robert S Walters, Jr.
(74) *Attorney, Agent, or Firm* — Pepper Hamilton LLP

(57) ABSTRACT

Functionalized copolymers of isoolefins and conjugated diolefins, methods of preparing the copolymers, and their use as compatibilizers are disclosed. The diolefin monomer units of the co-polymer are modified at the C—C double bond along the backbone of the copolymer to include an oxygen containing functional group such as epoxide, ester or alcohol. The functionalized copolymers improve the wettability of a non-hydrophilic surface towards hydrophilic polymer and allows for the formation of homogenous layers of the hydrophilic polymers. In particular, the spreading of a hydrophilic polymer on a non-hydrophilic substrate is
(Continued)

facilitated by applying the co-polymers as an interfacial layer between the two incompatible materials. The resulting coated substrates exhibit resistance to protein adsorption and cell growth after grafting. The co-polymers are especially suited in the coating of biomedical devices where a high degree of uniformity of the coated surface is required.

24 Claims, 10 Drawing Sheets

(51) Int. Cl.
| | |
|---|---|
| A61L 29/14 | (2006.01) |
| B05D 5/04 | (2006.01) |
| B05D 7/00 | (2006.01) |
| C08C 19/06 | (2006.01) |
| C09D 123/18 | (2006.01) |
| C09D 123/22 | (2006.01) |
| C09D 123/30 | (2006.01) |
| C08F 210/12 | (2006.01) |

(52) U.S. Cl.
CPC .............. *B05D 7/54* (2013.01); *C08C 19/06* (2013.01); *C09D 123/18* (2013.01); *C09D 123/22* (2013.01); *C09D 123/30* (2013.01); *A61L 2420/08* (2013.01); *B05D 2201/02* (2013.01); *B05D 2530/00* (2013.01); *C08F 210/12* (2013.01)

(56) References Cited

U.S. PATENT DOCUMENTS

| | | | |
|---|---|---|---|
| 5,077,352 | A | 12/1991 | Elton |
| 5,290,585 | A | 3/1994 | Elton |
| 5,306,246 | A | 4/1994 | Sahatjian et al. |
| 5,352,739 | A | 10/1994 | Arjunan |
| 6,270,902 | B1 | 8/2001 | Tedeschi et al. |
| 2003/0096911 | A1 | 5/2003 | Dias |

OTHER PUBLICATIONS

Dong, X.C., Preparation and Properties of Isobutylene-Isoprene Rubber Containing Multifunctional Groups, Iranian Polymer Journal, vol. 19, No. 10, pp. 771-779; Oct. 2010.

Bradbury, Howard J., Advances in the Epoxidation of Unsaturated Polymers, Ind. Eng. Chem. Res., 1988, 27, 2196-2203.

Schonhorn, H. "Surface Treatment of Polymers for Adhesive Bonding", Journal of Applied Polymer Science, vol. 1 1, pp. 1461-1474, 1967.

Haldar, S., "Grafting of Butyl Acrylate and Methyl Methacrylate on Butyl Rubber Using Electron Beam Radiation", Journal of Applied Polymer Science, vol. 101, pp. 1340-1346, 2006.

Yu, Q.S. "Optical Emission Diagnosticsd in Cascade Arc Plasma Polymerization and Surface Modification Processes", Journal of Polymer Science Part A, vol. 36, pp. 1583-1592, 1998.

Clough, R.L., "High-energy readiation and polymers: A review of commercial processes and emerging applications", ScienceDirect, vol. 185, Issues 1-4, Dec. 2001, pp. 8-33.

Bhowmick, A.K., "Electron Beam Curing of Elastomers", Rubber Chemistry and Technology: Jul. 2006, vol. 79, No. 3 pp. 402-428.

Bonduelle, C.V., "Patterning of a Butyl Rubber-Poly(ethylene oxide) Graft Copolymer Revealed by Protein Adsorption", American Chemical Society, Macromolecules, 2010, 43, pp. 9230-9233.

Jo, S. "Surface modification using silanated poly(ethylene glycol)s", Biomaterials, 21, 2000, pp. 605-616.

Shard, A., "Regenerative Medicine", vol. 1, No. 6, pp. 789-800, Nov. 2006.

Xigao, J., "Catalytic Epoxidation of Polyisobutylene-co-Isoprene with Hydrogen Peroxide", Journal of Polymer Science: Part A: Polymer Chemistry, vol. 29, pp. 547-553, 1991.

Guillen-Castellanos, S.A., "Synthesis of Ester Derivatives of Brominated Poly(isobutylene-co-isoprene): Solvent-Free Phase Transfer Catalysis", American Chemical Society, Macromolecules 2006, 39, pp. 2514-2520.

European Search Report from co-pending Application PCT/CA2011/050488, dated Oct. 18, 2011 2 pages.

\* cited by examiner

FUNCTIONALIZED COPOLYMERS OF ISOOLEFINS AND DIOLEFINS AND THEIR USE AS COMPATIBILIZERS

FIELD OF THE INVENTION

The present invention relates generally to functionalization of polymers, particularly copolymers of one or more isoolefin and one or more diolefin. The present invention also relates to use of these functionalized copolymers as compatibilizers.

BACKGROUND

In medical devices such as catheters, catheter inducers, guidewires and the like, it is often desirable to coat various plastic, rubber or metal parts thereof with products made from hydrophilic or certain other polymers that are lubricious and which produce low coefficients of friction during use. However, one of the problems associated with the utility of such coatings is their inability to remain intact and abrasion-resistant during clinical use in body fluids such as blood. Catheters used in angioplasty, gastroenterology and other medical specialties, are commonly made of polymeric materials which most often are relatively hydrophobic and not inherently slippery or biocompatible. Metal devices and components, such as guidewires to which permanent adhesion of slip agents and/or hydrophilic polymers is often desired, present additional challenges. In any case, polymeric and metallic substrates generally require some surface modification in order to reduce the friction between the catheter and other devices with which they work, such as vascular sheaths, and also to reduce the friction between the vasculature or other anatomical passageways and the catheter itself. Almost all currently used catheters have some form of surface modification or coating applied to them. The ability of the coating to reduce frictional resistance, its durability, as well as its biocompatibility are the most important functional aspects of an effectively coated surface.

It has been recognized that polymer surfaces can be provided with hydrophilic coatings formed by the combinations of certain polymers, both non-cross-linked and cross-linked, with a hydrophilic polymer like polyvinylpyrrolidone (PVP) or poly(ethylene oxide) (PEO). For example, U.S. Pat. Nos. 5,077,352, 5,160,790, 5,179,174 and 5,290,585 to ELTON each disclose a flexible, lubricious organic coating formed by applying a mixture of an isocyanate, a polyol, a hydrophilic polymer like poly(ethylene oxide) (PEO) or polyvinylpyrrolidone (PVP) and a carrier liquid to a surface to be coated. The carrier liquid is removed and the mixture reacted to form a lubricous, flexible homogenous coating of crosslinked polyurethane linkages complexed with PVP or PEO particularly suitable for use as a protective lubricous coating on medical devices introduced into the body.

The use of a crosslinked polyurethane complexed with poly(ethylene oxide) (PEO) or polyvinylpyrrolidone (PVP) has proven to be an effective, lubricous and durable coating on numerous organic substrates. However, there are several organic substrates and numerous inorganic and organometallic substrates (glass, ceramic, metal, silicone, etc.) that first require surface treatment/modification to provide an effective lubricous, durable coating when aforementioned polyurethane complexed with PEO or PVP coatings are applied.

The crosslinked polyurea/PEO or PVP coatings are generally formed from the curing of the product resulting from the reaction of an isocyanate and a compound having at least two active hydrogens per molecule selected from the group consisting of polyamines, polymercaptans, and polycarboxylates or compounds with NH, $NH_2$, SH or COOH groups on the same molecule, in the presence of the hydrophilic PEO or PVP polymer.

Polymers such as butyl rubber are commercial elastomers with many desirable properties including high elasticity, impermeability to gas and water, damping characteristics, and chemical stability. However, due to its nonpolar nature, evidenced by its relatively high surface contact angle of approximately 90°, it is widely recognized to have poor compatibility with more polar polymers and materials. In particular, spreading of more hydrophilic materials on the polymer surface during a coating process is not easily achieved in a uniform manner. The incompatibility between two different materials with two different properties, hydrophilic and hydrophobic can create partial or complete dewetting after casting of the coating. Consequently, the obtained non-homogeneous layer is not suitable for physical grafting using processes such as plasmas or hyperthermal hydrogen induced cross-linking (HHIC). The resulting surfaces are not suitable for high end applications such as biomedical, where a high degree of control over the surface and its uniformity is required.

There are many examples describing the use of hydrophilic polymers (such as PEO) coated surfaces to resist the adsorption of protein. Many of these examples involve the chemical attachment of functionalized hydrophilic polymers to the surface. These methods cannot be applied directly to polymer surfaces that do not inherently have reactive chemical functionalities. For example, butyl rubber, which is composed almost entirely of C—C, and C—H bonds with only a small percentage of C=C bonds from the isoprene units. Physical treatments such as plasma or electron beam can be used, but they generally require the coating of the surface with the hydrophilic polymers such as PEO. The incompatibility of hydrophobic or non-polar or less polar polymer surfaces with hydrophilic or more polar polymers, results in poor wetting. Therefore, for use of these physical treatment methods, it is important to resolve the wettability problem.

Haldar and Singha (*J. Appl. Polym. Sci.* 2006, 101, 1340-1346) have described the grafting of butyl acrylate and methyl methacrylate on butyl rubber surfaces using electron beam radiation (i.e., polymerization from the surface) as a means to potentially enhance compatibility of butyl with other polymers. No compatibility properties were investigated and based on their microscopy images, their layers of PMMA deposited on the surface do not appear to be uniform.

U.S. Patent Publication Nos. 2002/0028883 A1 and 2003/0096911 A1 describe the production of compatibilized blends of general purpose rubbers and benzyl halide polymers through the solventless reaction of a multifunctional reagent that reacts with the benzylic halide in one polymer and the diene in the other polymer. U.S. Patent Publication No. 2008/0214669 A1 also discloses a similar approach. These approaches are aimed at the bulk blending of materials, and involve specific chemical reactions between the two polymers. U.S. Pat. No. 5,352,739 describes a process for compatibilizing polar/nonpolar rubber blends using compatibilizer additives such as ethylene/vinyl acetate or ethylene/methacrylate copolymers. There are many other examples of compatibilization methods for the blending of bulk materials.

U.S. Pat. No. 6,270,902 describes a method for improving the adherence or bonding of lubricious coatings including PEO on a variety of surfaces, including mention of commercial rubbers. This method involves a 2-step process where the first step is the high energy treatment such as plasma, or corona and electron discharges to etch the surface and deposit reactive functional groups. The next step involves the chemical reaction of these functional groups with a suitable functionalized PEO derivative. The method disclosed in this patent is based on specific chemical reactions between the layers. This patent, however, does not provide any data on protein adsorption or cell growth on the coated polymer surfaces discloses therein.

SUMMARY OF THE INVENTION

It is an object of the present invention to provide functionalized copolymers of isoolefins and diolefins as compatibilizers. In accordance with an aspect of the present invention there is provided a method of improving wettability of a substrate surface towards a hydrophilic polymer, comprising applying a compatibilizer to the surface, the compatibilizer comprising a functionalized copolymer comprising repeating units derived from at least one C4-C8 isoolefin and units derived from at least one C4-C16 conjugated diolefin, wherein the copolymer comprises one or more units derived from the at least one conjugated diolefin wherein the C—C double bond along the backbone of the copolymer is functionalized with an oxygen containing functional group.

In accordance with an aspect of the present invention there is provided a method of coating a hydrophilic polymer on a non-hydrophilic substrate, the method comprising the steps of a) applying a compatibilizer on a surface of the substrate to form an interfacial layer; wherein the compatibilizer comprises a functionalized copolymer comprising repeating units derived from at least one C4-C8 isoolefin and units derived from at least one C4-C16 conjugated diolefin, wherein the copolymer comprises one or more units derived from the at least one conjugated diolefin wherein the C—C double bond along the backbone of the copolymer is functionalized with a oxygen containing functional group, and b) applying a hydrophilic polymer onto the interfacial layer obtained in step a).

In accordance with an aspect of the present invention there is provided a compatibilizer comprising a functionalized copolymer comprising repeating units derived from at least one C4-C8 isoolefin and repeating units derived from at least one C4-C16 conjugated diolefin, wherein the copolymer comprises one or more units derived from the at least one conjugated diolefin wherein the C—C double bond along the backbone of the copolymer is functionalized with an oxygen containing functional group.

DETAILED DESCRIPTION OF THE INVENTION

Definitions

Figure 1:
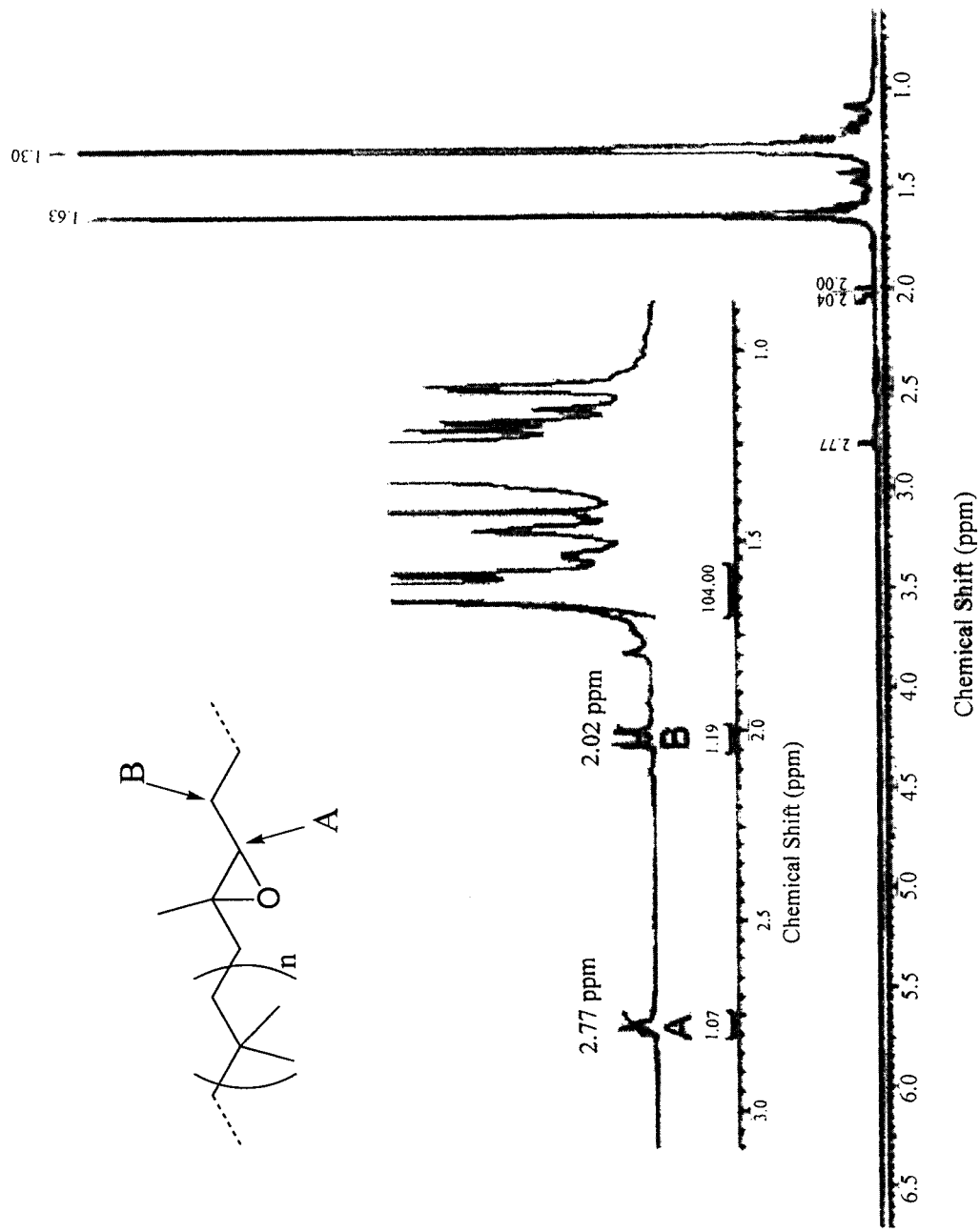
FIG. 1 relates to $^1$H NMR spectrum of epoxidized butyl rubber 2 (in $C_6D_6$)
Figure 2:
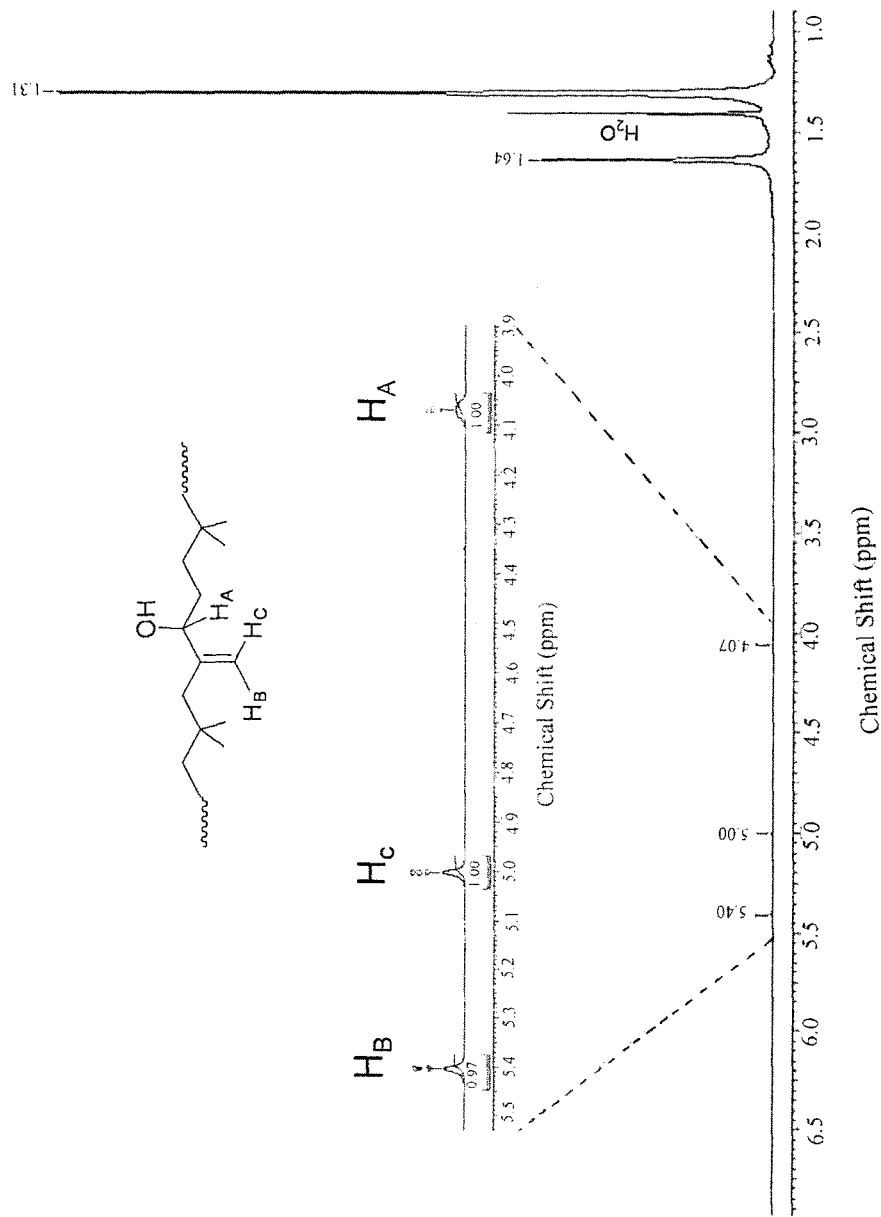
FIG. 2 relates to $^1$H NMR spectrum of the hydroxyl functionalized butyl rubber 3 (in $C_6D_6$)
Figure 3:
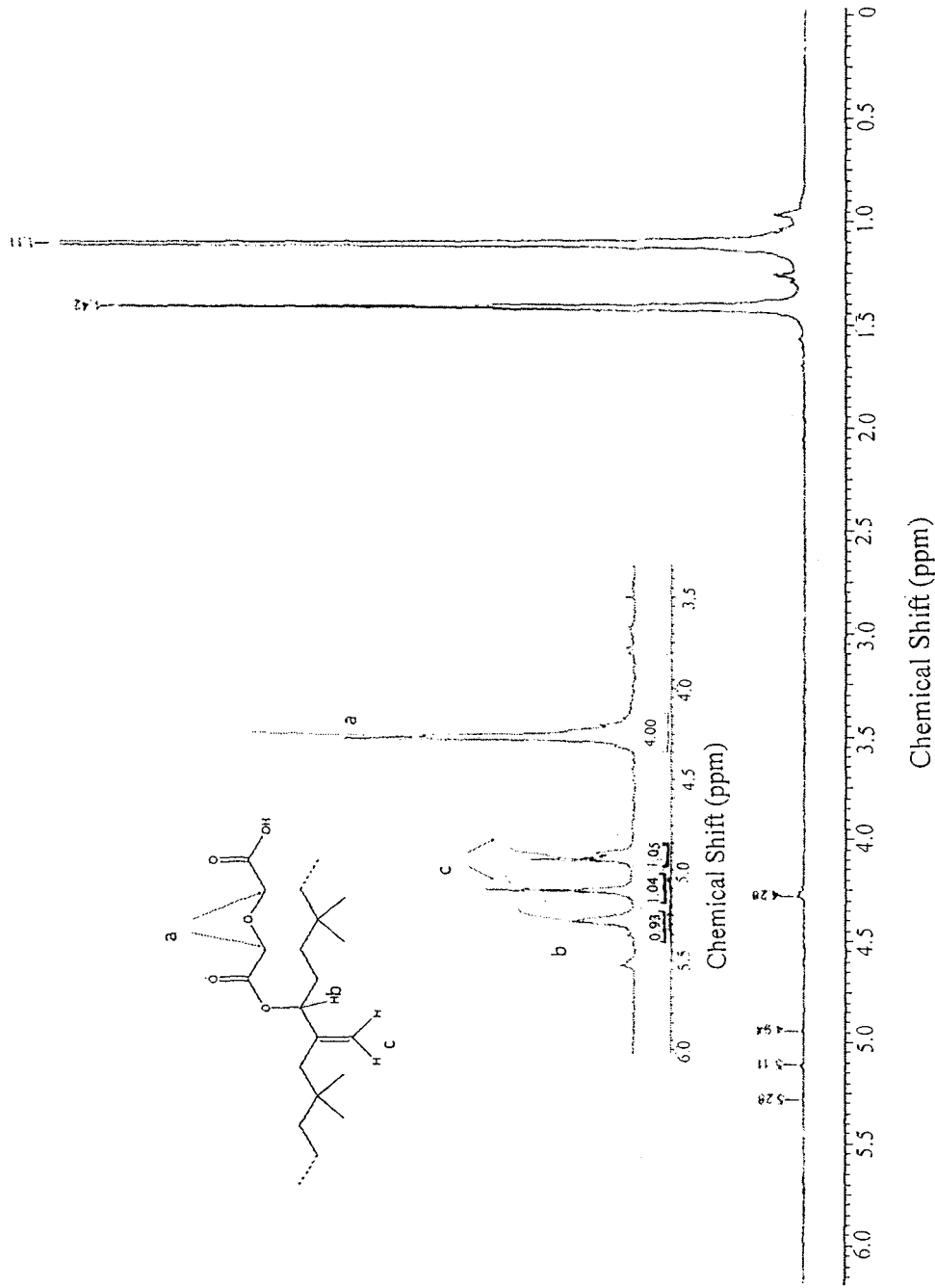
FIG. 3 shows $^1$H NMR spectrum of the carboxylic acid functionalized butyl rubber 4 (in $CDCl_3$)

The term "hydrophobic polymer" as used herein relates to any polymer resistant to wetting, or not readily wet, by water, i.e., having a lack of affinity for water. Such polymers can be substantially free of polar functional groups.

Examples of hydrophobic polymers include, by way of illustration only, polyolefins and copolymers of olefins, such as polyethylene, poly(isobutene), poly(isoprene), poly(4-methyl-1-pentene), polypropylene, isobutylene-isoprene copolymers, ethylene-propylene copolymers, ethylene-propylene-hexadiene copolymers, and ethylene-vinyl acetate copolymers; metallocene polyolefins, such as ethylene-butene copolymers and ethylene-octene copolymers; styrene polymers, such as poly(styrene), poly(2-methylstyrene), etc.

The term "hydrophilic polymer" as used herein relates to any polymer having affinity for water. Such polymers comprise polar or charged functional groups.

Examples of hydrophilic polymers include polyvinylstearate (PVS), poly(methyl methacrylate) (PMMA), polycaprolactone (PCL), and poly(ethylene oxide) (PEO)/poly(ethylene glycol) (PEG), polyvinyl alcohol (PVA), polypropylene glycol, di- and tri-block copolymers of polyethylene glycol and polypropylene glycol, and any combination thereof.

The term "wettability" used herein relates to the ability of any solid surface to be wetted when in contact with water or hydrophilic liquid or a hydrophilic polymer, that is, the surface tension of the liquid is reduced so that the liquid spreads over the surface.

Alternatively, wetting is the ability of a liquid, such hydrophilic polymer solution to maintain contact with a solid surface, resulting from intermolecular interactions when the two are brought together. The degree of wetting (wettability) is determined by a force balance between adhesive and cohesive forces.

The present invention relates to functionalized copolymers of one or more isoolefins and one or more diolefins, methods of preparing these copolymers, and their use as compatibilizers to improve wettability of substrates towards hydrophilic materials.

Functionalized Graft Co-polymers

The functionalized copolymers of the present invention comprise repeating units derived from at least one isoolefin and repeating units derived from at least one conjugated diolefin. The term "functionalized copolymer" as used herein defines a copolymer comprising one or more units derived from isoolefin and one or more units derived from the at least one conjugated diolefin wherein one or more C—C double bonds along the backbone of the copolymer are converted into an epoxide group or a C—C single bond having an oxygen containing functional group on at least one of the carbon atoms.

The non-limiting examples of the oxygen containing functional group are epoxide, hydroxyl, or —OC(O)—R, wherein R is H; $C_{1-6}$ alkyl; $C_{1-6}$ alkyl substituted with —O—$C_{1-6}$ alkyl, —C(O)R' or —O—$C_{1-6}$ alkyl-C(O)R', where R' is H, OH, $C_{1-6}$ alkyl or —O—$C_{1-6}$ alkyl.

In one embodiment, the oxygen containing functional group is —OC(O)—R, wherein R is H, $C_{1-6}$ alkyl, optionally substituted with —O—$C_{1-6}$ alkyl, —C(O)R' or —O—$C_{1-6}$ alkyl-C(O)R', where R' is H, OH, $C_{1-6}$ alkyl or —O—$C_{1-6}$ alkyl.

In one embodiment, the oxygen containing functional group is —OC(O)—R, wherein R is $C_{1-6}$ alkyl substituted with —C(O)R' or —O—$C_{1-6}$ alkyl-C(O)R', where R' is H, OH, $C_{1-6}$ alkyl or —O—$C_{1-6}$ alkyl.

In one embodiment the oxygen containing functional group is —OC(O)—R, wherein R is —CH$_2$—O—CH$_2$—C(O)R', —CH$_2$—CH$_2$—CH$_2$—C(O)R' or —CH$_2$—CH$_2$—C(O)R', wherein R' is OH or —O—$C_{1-6}$ alkyl.

In one embodiment, the functionalized copolymer comprises one or more units represented by the formula:

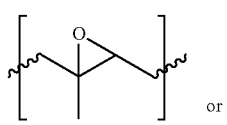

(I)

or

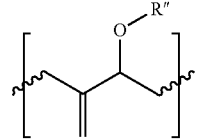

(II)

wherein R" is H or —C(O)—R, wherein R is H; $C_{1-6}$ alkyl; or $C_{1-6}$ alkyl substituted with —O—$C_{1-6}$ alkyl, —C(O)R' or —O—$C_{1-6}$ alkyl-C(O)R', where R' is H, OH, $C_{1-6}$ alkyl or —O—$C_{1-6}$ alkyl.

In one embodiment, the functionalized copolymer of the present invention has a weight average molecular weight of about 250000 to about 1500000 g/mol.

In one embodiment, the conjugated diolefin units in the copolymer of the present invention have 4 to 8 carbon atoms.

In one embodiment, the conjugated diolefin is isoprene.

In one embodiment, the unfunctionalized copolymer comprises one or more isoprene units represented by the formula (III):

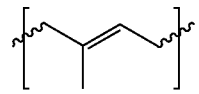

(III)

In one embodiment, the functionalized copolymer of the present invention comprises randomly repeating units a and b represented by the formula (IV):

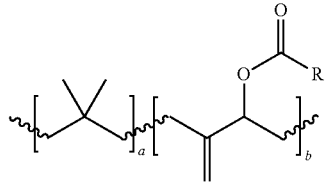

(IV)

wherein the combination of a+b represents the empirical formula of substantially random graft copolymer, wherein the ratio of a:b is [about 10 to about 2000]: [about 1 to about 200], and R is H, $C_{1-6}$ alkyl, optionally substituted with —O—$C_{1-6}$ alkyl, —C(O)R' or —O—$C_{1-6}$ alkyl-C(O)R', where R' is H, OH, $C_{1-6}$alkyl or —O—$C_{1-6}$ alkyl.

In one embodiment, in the copolymer represented by formula (IV), R is $C_{1-6}$ alkyl substituted with —C(O)R' or —O—$C_{1-6}$ alkyl-C(O)R', where R' is H, OH, $C_{1-6}$ alkyl or —O—$C_{1-6}$ alkyl.

In one embodiment, in the copolymer represented by formula (IV), R is —CH$_2$—O—CH$_2$—C(O)R', —CH$_2$—CH$_2$—CH$_2$—C(O)R' or —CH$_2$—CH$_2$—C(O)R', wherein R' is OH or —O—$C_{1-6}$ alkyl.

In one embodiment, the functionalized copolymer of the present invention is represented by the formula:

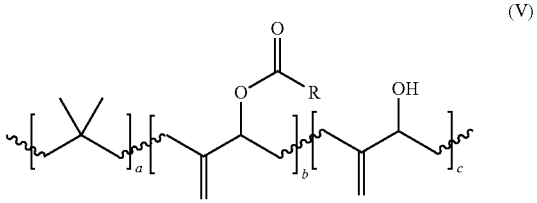

(V)

wherein the combination of units a+b+c represents the empirical formula of substantially random graft copolymer, wherein unit a ranges from about 10 to about 2000, unit b ranges from about 1 to about 200, and unit c is 0 to about 200, and d is 0 to about 200, and R is as defined above for formula (IV).

Preparation of Functionalized Graft Copolymers

The functionalized graft copolymers of the present invention can be prepared by epoxidizing the one or more C—C double bonds along the back bone of the copolymer to form a copolymer functionalized with an epoxy group. The epoxidized copolymer can then be treated with a protic acid to undergo ring opening of one or more epoxides to form one or more hydroxyl groups. The hydroxyl functionalized copolymer can then be treated with a reagent that can convert the hydroxyl groups into an ester groups.

The esterification reagent can be represented by the formula:

R—C(O)—R''' wherein R is H; $C_{1-6}$ alkyl; or $C_{1-6}$ alkyl substituted with —O—$C_{1-6}$ alkyl, —C(O)R' or —O—$C_{1-6}$ alkyl-C(O)R', where R' is H, OH, $C_{1-6}$ alkyl or —O—$C_{1-6}$ alkyl, and R''' is:

—OH, —O-alkyl, , —$OCX_3$,

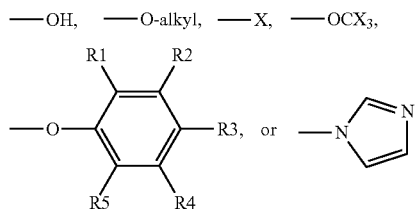

wherein X is halogen, R1 to R5 are each independently H, $NO_2$, halogen or C1-C6 alkyl;

Alternatively, R and R''', taken together with the C(O) group form a cyclic C4-C6 alkyl anhydride, wherein one or more carbon atoms are optionally replaced with an oxygen atom;

In one embodiment, the esterification reagent is an acid anhydride. Non limiting examples as acid anhydride are diglycolic anhydride, glutaric anhydride, succinic anhydride, etc.

The epoxidation step can be carried out using peroxide reagents known in the art. Non limiting examples of such reagents are hydrogen peroxide, peroxycarboxylic acids (generated in situ or preformed), alkyl hydroperoxides, and dimethyldioxirane. In one embodiment, the epoxidizing agent is perbenzoic acid or m-chloroperbenzoic acid.

The protic acids used in the epoxide ring opening step can be selected from the group consisting of HCl, HBr, HF, $H_2SO_4$, and $HNO_3$.

The solvents used in the epoxidation step, in the ring opening of the epoxide and/or in the esterification step can be any solvent that solubilizes the copolymer. Non-limiting examples of such solvents are toluene, hexanes, chloroform, dichloromethane or tetrahydrofuran.

The un-functionalized copolymers used in the present invention comprise from about 0.5 to about 20 mol % of the repeating units derived from the conjugated diolefin and about 80 to about 99.5 mol % of repeating units derived from isoolefin. In one embodiment, the conjugated diolefin units are from about 0.5 to about 10 mol % of the copolymer. In one embodiment, the conjugated diolefin units are from about 1 to about 8 mol %.

The un-functionalized copolymers used in the present invention have a weight average molecular weight of about 250000 to about 1500000 g/mol. In one embodiment, the weight average molecular weight of the un-functionalized copolymers is 350000 or 1000000.

The isoolefins suitable for use in the present inventions are hydrocarbon monomers having about 4 to about 10 carbon atoms. Illustrative non-limiting examples of these isoolefins are isobutylene, 2-methyl-1-butene, 3-methyl-1-butene, 2-methyl-2-butene, 2-methyl-1-pentene or 4-methyl-1-pentene. In one embodiment, the isoolefin is isobutylene.

The conjugated diolefin for use in the methods of the presently claimed invention can be represented by a general formula:

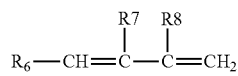

wherein R6 is a hydrogen atom or an alkyl group containing in the range from 1 to 4 carbon atoms and wherein R7 and R8 can be the same or different and are selected from the group consisting of hydrogen atoms and alkyl groups containing in the range from 1 to 4 carbon atoms.

In one embodiment, of the above formula one of R7 and R8 is other than H.

Some representative non-limiting examples of suitable conjugated diolefins include 1,3-butadiene, isoprene, 2-methyl-1,3-pentadiene, 4-butyl-1,3-pentadiene, 2,3-dimethyl-1,3-pentadiene 1,3-hexadiene, 1,3-octadiene, 2,3-dibutyl-1,3-pentadiene, 2-ethyl-1,3-pentadiene, 2-ethyl-1,3-butadiene and the like.

In one embodiment, the conjugated diolefins used in the method of the present invention have 4 to 8 carbon atoms.

In one embodiment, the conjugated diolefin is isoprene.

In one embodiment, the un-functionalized copolymer comprises one or more isoprene unit represented by the formula:

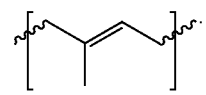

In the functionalization process, one or more of the isoprene units as shown above are converted into one or more allylic hydroxyl sites, represented by the formula:

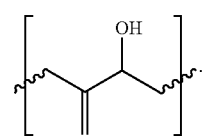

The allylic hydroxide containing isoprene units (i.e., allylic hydroxyl sites) are then converted into one or more functionalized isoprene units represented by the formula:

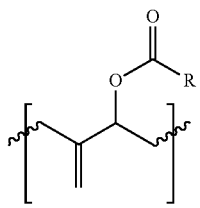

wherein R is as defined above.

In one embodiment, the un-functionalized copolymer is a butyl rubber. In one embodiment the butyl rubber is butyl rubber RB402, butyl rubber RB100 or butyl rubber RB301.
Functional Copolymers as Compatibilizers In one embodiment, the functionalized copolymers of the present invention can be used as compatibilizers for improving wettability of a substrate surface towards a hydrophilic materials, by applying these copolymers onto the surfaces. The hydrophilic materials can then be applied onto the compatibilizer treated substrates to form homogenous layers of the hydrophilic materials.

In one embodiment, the hydrophilic material is one or more hydrophilic polymers. Non limiting examples of hydrophilic polymers include PEO, PMMA, polyesters, PVA, etc.

The compatibilizers of the present invention can be applied onto inorganic or organic substrates. The examples of inorganic substrates are metal, glass, ceramic and silicon materials.

The organic substrate can be a polymeric substrate comprising one or more hydrophobic or less polar polymers. In one embodiment, the substrate can be an inorganic substrate coated with a hydrophobic or less polar/non-polar polymer layer. In one embodiment, the hydrophobic polymer is butyl rubber. In one embodiment, the substrate is one or more sheets of cured butyl rubber or cross-linked films of spin cast butyl rubber.

In one embodiment, the present invention relates to method of coating a hydrophilic/polar polymer on a non-hydrophilic (i.e., hydrophobic/less hydrophilic/non-polar/neutral substrate), which comprises the steps of applying the compatibilizer of the present invention on a substrate surface to form an interfacial layer; and then applying a hydrophilic polymer onto the interfacial layer.

In one embodiment, the compatibilizers can be applied as solution in a solvent which solubilizes the compatibilizer. Non limiting examples of compatibilizer solubilizing solvents are hexane, chloroform, dichloromethane, tetrahydrofuran, toluene, chlorobenzene, acetone, etc.

In one embodiment, the hydrophilic polymers can be applied as a solution in a solvent which solubilizes the hydrophilic polymer. Non limiting examples of hydrophilic polymer solubilizing solvents are chloroform, dichloromethane, tetrahydrofuran, N,N-dimethylformamide, ethyl acetate, toluene, chlorobenzene, acetone, etc.

The compatibilizers and/or the hydrophilic polymers can be applied onto the surfaces via spin coating, dip coating or spray coating methods as known in the art.

In one embodiment, the polymer layers after applying the compatibilizer and/or after applying the hydrophilic polymer are cross linked with the substrate layer they are applied onto. The crosslinking can be achieved by methods such as Hyperthermal Hydrogen Induced Crosslinking (HHIC) as described in PCT Publication No. WO 2010/099608, crosslinking with activated species from Inert Gas-Casing known in the art (Schonhorn et. al. in H. J. Appl. Polym. Sci. 2003, 11, 1461-1474, Yu, et. Al., J. Polym. Sci., Part A: Polym. Chem. 1998, 36, 1583-1592, and Yasuda, H. K.; Lin, Y. S.; Yu, Q. S. Prog. Org. Coat. 2001, 42, 236-243, or electron beam crosslinking (Clough R. L., Nucl. Instr. Meth. Phys. Res. B, 2001, 185, 8-33; Chmielewski A. G., Haji-Saeid M., Ahmed S., Nucl. Instr. Meth. Phys. Res. B, 2005, 236, 44-54; and Browmick A. K., Vijayabaskar V., Rubb. Chem. Technol., 2006, 79, 402-428), incorporated herein by reference.

The functionalized copolymers of the present invention improve the wettabilty of surfaces towards hydrophilic polymers, and allow the formation of homogenous layers of the hydrophilic polymers as compared to surface not coated with these compatibilizers. The hydrophilic polymer coated substrates, produced using the compatibilizers of the present invention, exhibit resistance to protein adsorption and cell growth after grafting.

The invention will now be described with reference to specific examples. It will be understood that the following examples are intended to describe embodiments of the invention and are not intended to limit the invention in any way.

Materials:

Silicon wafers were purchased from University Wafer (Boston, USA). Butyl rubber RB402 (weight-average molecular weight $M_w$ of 400000 g/mol) composed of 2.2 mol % of isoprene units was obtained from LANXESS. Solvents were purchased from Caledon and all other chemicals were purchased from Sigma Aldrich and were used without further purification unless otherwise noted. 4-(Dimethylamino)pyridine (DMAP) was purified by recrystallization in toluene before use. m-Chloroperbenzoic acid was dissolved in toluene and dried with $MgSO_4$ before use. Dry toluene was obtained from a solvent purification system. $^1H$ NMR spectra were obtained in $CDCl_3$ at 400 MHz or 600 MHz. NMR chemical shifts are reported in ppm and are calibrated against residual solvent signals of $C_6D_6$ or $CDCl_3$ (δ 7.16, 7.26). Coupling constants (J) are reported in Hz.

General Procedures:
Molecular Weight Determination:

Molecular weights are determined by Size exclusion chromatography (SEC), carried out in THF or $CHCl_3$ using a Waters 2695 separations module equipped with a 2414 differential refractometer and two Resipore (300 mm×7.5 mm) columns from Polymer Laboratories. The calibration was performed using polystyrene standards.

Hydrophilic Polymer Coating on Surfaces:

Thin films of hydrophilic polymer on butyl rubber were prepared by spin coating a solution (2.5 or 5 mg/mL, 100 μL for 1 cm², 6000 rpm, 30 s) of the hydrophilic polymer in $CH_2Cl_2$ (PEO, PMMA, PCL, PVA) on a butyl rubber or compatibilizer coated silicon wafer. The surfaces were then cross-linked using HHIC.

Hyperthermal Hydrogen Induced Cross-linking (HHIC)

The surfaces were treated with hyperthermal hydrogen for the modified silicon wafers or butyl rubber specimens, with a treatment time of 30 seconds to 100 s. For the butyl rubber surfaces, the spin coated and cross-linking steps were carried out twice. The conditions were: (a) the hydrogen plasma was maintained with 200 W of microwave energy, and 87.5 mT in magnetic field for increasing the plasma density; (b) protons were extracted by a grid electrode at −96V, into the draft tube of 50 cm at 0.80 mTorr of gaseous hydrogen; and (c) ions and electrons were screened in front of the specimen with a pair of grid-electrodes biased to +60 V and −40V. Under this set of conditions, a high flux of hyperthermal neutral hydrogen projectiles, with appropriate kinetic energy to break C—H bonds but not other bonds undesirably, was delivered to the specimen surface.

AFM Analyses:

Method A: Surface morphology of the samples was imaged with the dynamic force mode using a Park Systems XE-100 atomic force microscope. A rectangular-shaped silicon cantilever (T300, VISTAprobes) was used, which has a nominal tip apex radius of 10 nm, spring constant of 40 N/m and resonant frequency of 300 kHz. The cantilever was vibrated around its resonant frequency and its reduced amplitude was used as the feedback parameter to image the sample surface. The measurements were carried out in air at room temperature.

Method B: Surfaces were visualized by an atomic force microscope (Nanoscope III AFM system Digital Instrument). Images were obtained by scanning the surface in a tapping mode using rectangular-shaped silicon cantilevers with a spring constant of 48 N/m. Data were then refined using the software Nanoscope and digitally obtained scans were graphically modified by using the software Gwyddion.

Contact Angle Measurements:

A contact angle goniometer (Ramé-Hart's Model 100-00 or Kress DSA 100) was used. Surfaces were first loaded onto the stage and drops of distilled water were placed on the specimens. The reported static angles were calculated by averaging the angles from both the left and right sides of the droplet. Advanced and receding contact angles were also evaluated. At least 10 measurements on each surface were obtained for each experimental condition.

Preparation of Control Surfaces for Protein Adsorption Test:

Thin films of PEO were prepared by spin coating a solution of PEO in $CH_2Cl_2$ (4 mg/mL, 100 μL for 1 $cm^2$, 6000 rpm, 30 s) on a clean silicon wafer. The films were cross-linked by HHIC treatment for 100 s. PEO grafted glass surfaces were prepared by silanation of glass surfaces with (N-triethoxysilylpropyl)-O-monomethoxy PEG urethane in ethanol.

Protein Adsorption:

A solution of a Rhodamine-fibrinogen conjugate in 5 mM phosphate buffer, pH 7.2 was prepared at a concentration of 400 μg/mL. The surfaces were then immersed in the protein solution. After 2 hours, the non-adsorbed protein was removed by washing the surfaces with buffer and water. The fluorescence was then evaluated by using an LSM 510 multi-channel point scanning confocal microscope (Laser 543 nm and band pass filter of 560-600 nm). The fluorescence was evaluated by averaging 10 randomly selected regions of the surface within each sample. Linear operation of the camera was ensured, and the constant exposure time used during the image collection permitted quantitative analyses of the observed fluorescent signals. The fluorescence microscopy images were analyzed using the software Northern Eclipse Image Analysis (Empix Imaging, Mississauga, Ontario) which yielded the mean and standard deviation of the fluorescence intensity within a given image. The fluorescence intensity of a region of the surface that was not exposed to protein was measured in order to quantify the background fluorescence of the material itself and this value was subtracted from the fluorescence measured for the exposed regions. The background-corrected fluorescence intensity for each film was then used to compare the protein adsorption on each surface. For all the samples, three surfaces were prepared and measured.

Preparation of Surfaces for Evaluation of Cell Growth

A sheet of bulk cured butyl rubber 08CA361 was washed by immersion in water for 24 h and then cut and sterilized by UV light (1 h). This washed sheet of butyl rubber was also spin coated with epoxidized butyl rubber in hexane (5 mg/mL, 100 μL for 1 $cm^2$, 6000 rpm, 30 s) followed by PEO in $CH_2Cl_2$ (4 mg/mL, 100 μL for 1 $cm^2$, 6000 rpm, 30 s) twice. The control PEO-coated surfaces were prepared as described above for the protein adsorption test.

Evaluation of Cell Growth $C_2C_{12}$ mouse myoblast cells were cultured in growth medium composed of Dulbecco's Modified Eagle Medium (DMEM) containing 10% fetal bovine serum (FBS) and supplemented with 1% Glutamax (100×) solution and 1% Penstrep (100×). $1\times10^4$ cells were seeded on each of the prepared surfaces (1 $cm^2$). These cells were incubated in the growth medium described above at 37° C. (5% $CO_2$). After 48 hours, the growth medium was aspirated and the surfaces were washed 3 times with PBS (pH=7.2). The cells were then incubated for 10 minutes with a para-formaldehyde fixing solution (400 mg in 10 mL of PBS 10×, pH=7.2) and then washed 3 times with PBS (pH=7.2). After fixation, the surfaces were immersed in cold acetone (3 min) and in PBS buffer (10 min) for permeation. Finally, the surfaces were immersed in a DAPI solution (1 μg/mL in water) to stain the cell nuclei. The number of cells on each surface was then evaluated by fluorescence microscopy. Ten randomly selected regions were averaged for each surface. For each sample, three surfaces were prepared and measured.

General Reaction Schemes:

The reaction sequences used in the preparation of examples of functionalized copolymers of the present application is shown below in Scheme 1:

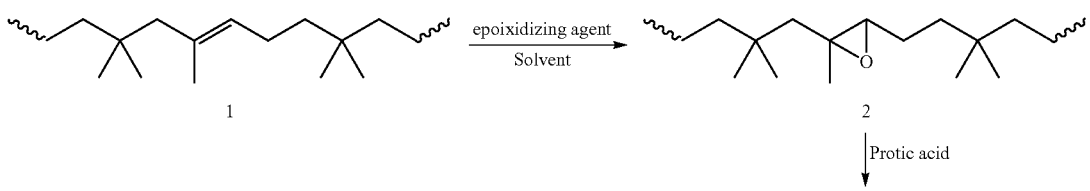

-continued

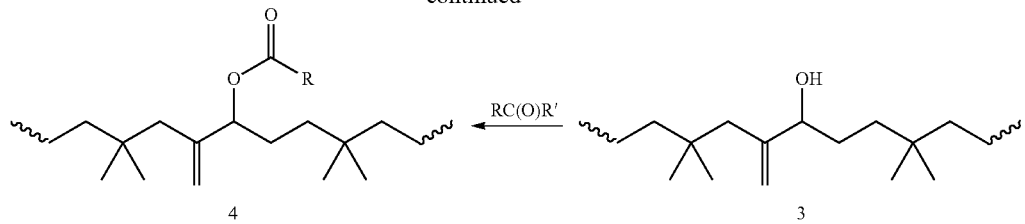

EXAMPLE 1

Synthesis of Epoxidized butyl Rubber (2)

Butyl rubber (1) (11 g, 4.3 mmol of isoprene units) was dissolved in dry toluene (300 mL). A previously dried solution of meta-chloroperoxybenzoic acid (6.0 g in 180 mL of toluene) was added to the poly(isobutylene-co-isoprene) in solution. The resulting mixture was stirred overnight at room temperature. After evaporation of the solvent in vacuo, epoxidized butyl rubber was purified by precipitation in acetone/toluene (2:1) twice. The resulting polymer (2) was dried under vacuum (yield 91%). $^1$H NMR (400 MHz, benzene $D_6$): δ 2.77 (t, 1H, J=5.8 Hz), 1.63 (s, $CH_2$ polyisobutylene, 88H), δ 1.30 ppm (s, $CH_3$ polyisobutylene, 264H). SEC: $M_w$=433000 g/mol, PDI=2.17.

EXAMPLE 2

Synthesis of hydroxylated butyl Rubber (3)

Butyl rubber (2) (10 g, 3.9 mmol of epoxidized units) was dissolved in toluene (300 mL). An aqueous HCl solution (37%, 530 µL 6.4 mmol) was added and the reaction was stirred overnight at room temperature. After evaporation of the solvent in vacuo, hydroxylated butyl rubber (3) was purified by precipitation in acetone/toluene (2:1) twice. The resulting polymer was dried under vacuum (yield 90%). $^1$H NMR (400 MHz, benzene $D_o$): δ 5.40 (s, 1H), 5.00 (s, 1H), 4.05-4.09 (m, 1H), 1.63 (s, $CH_2$polyisobutylene, 88H), 1.30 (s, $CH_3$polyisobutylene, 264H). SEC: $M_w$=391200 g/mol, PDI=2.16.

EXAMPLE 3

Synthesis of Acid Functionalized butyl Rubber (4)

Butyl rubber (3) (10 g, 3.9 mmol of hydroxylated units) was dissolved in toluene (300 mL). A solution of diglycolic anhydride was prepared by dissolving 10 equivalents of the anhydride (4.5 g, 39 mmol) in toluene (200 mL). The hydroxylated butyl rubber was heated to 75° C. To the solution, 2 equivalents of 4-dimethylaminopyridine (0.95 g, 7.8 mmol) were added, followed by 20 equiv. of triethylamine (10.9 mL). The anhydride solution was added via syringe and the reaction was stirred overnight at 95° C. The reaction mixture was washed twice with 6 M HCl, then the solvent was evaporated. The product was purified by precipitation in acetone/toluene (2:1) twice, then was dried under vacuum (yield 90%). $^1$H NMR (400 MHz, CDCl$_3$): δ 5.29 (br s, 1H), 5.12 (s, 1H), 4.95 (s, 1H), 4.20-4.40 (m, 4H), 1.42 (s, $CH_2$ polyisobutylene, 174 H), 1.12 (s, $CH_3$ polyisobutylene, 431 H). SEC: M, =309000 g/mol, PDI=2.52.

EXAMPLE 4

Preparation of Surfaces for Applying Compatibilizer of the Present Invention 4a: Preparation of Silicon Surfaces:

Silicon wafers were cleaned by immersion in $H_2O_2$/$H_2SO_4$ solution. They were then rinsed with deionized distilled water and dried at 100° C.

4b: Preparation of butyl Rubber Surface:

Thin films of butyl rubber were prepared by spin coating a solution of butyl rubber RB 402 in hexane (5 mg/mL, 100 µL, for 1 cm$^2$, 6000 rpm, 30 s) on a clean silicon wafer. The surface was cross-linked by HHIC.

EXAMPLE 5

Preparation of Compatibilizer-coated Surfaces

Thin films of oxygenated butyl rubber derivatives 2, 3, or 4 were prepared by spin-coating a solution of these derivatives in hexane (5 mg/mL, 100 µL for 1 cm$^2$, 6000 rpm, 30 s) on a clean silicon wafer or on a butyl rubber coated silicon wafer.

Figures 4A, 4B, 4C, 4D, 4E:
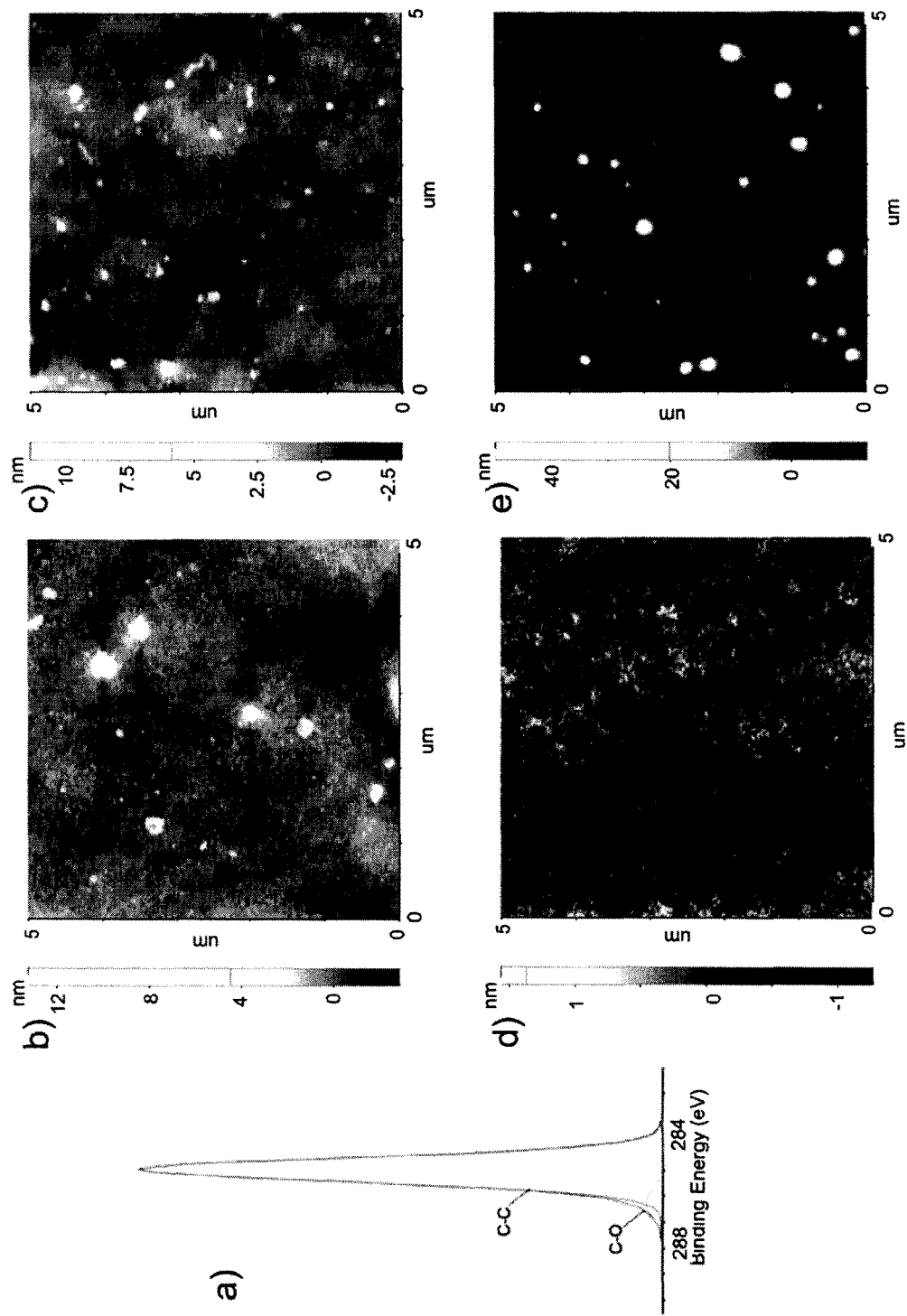
FIG. 4a shows high resolution X-ray photoelectron spectroscopy (XPS) $C_{1S}$ of the epoxidized butyl thin film coated onto butyl rubber.
FIG. 4b shows AFM image (topography) of a thin film of cross-linked butyl rubber.
FIG. 4c shows AFM image (topography) of a thin film of crosslinked epoxidized butyl rubber 2 coated on butyl rubber.
FIG. 4d shows AFM image (topography) of a thin film of crosslinked hydroxyl functionalized butyl rubber 3 coated on butyl rubber.
FIG. 4e shows AFM image (topography) of a thin film of crosslinked acid functionalized butyl rubber 4 coated on butyl rubber.

High resolution X-ray photoelectron spectroscopy (XPS) $C_{1S}$ spectra confirmed the presence of the epoxide functionality when thin films of the butyl derivative 2 was coated onto the surface, for example FIG. 4A showing XPS $C_{1S}$ spectra of the epoxidized butyl 2 thin film coated onto butyl rubber, suggested that the epoxidized.

EXAMPLE 6

Physical Grafting and Characterization of Oxygenated butyl Rubber

The films of epoxidized butyl rubber were grafted onto the butyl rubber surface by using HHIC. XPS results suggested that the epoxy groups survived the HHIC treatment process (FIG. 4A), and atomic force microscopy (AFM) demonstrated that uniform films of epoxy butyl rubber on butyl rubber could be obtained (FIGS. 4B, and 4C). Similarly, FIGS. 4D and 4E show AFM image (topography) of a thin film of crosslinked hydroxyl functionalized butyl rubber 3 and crosslinked acid functionalized butyl rubber 4, respectively coated on butyl rubber. The measurements for film thickness, roughness, and contact angles are shown in Table 1.

TABLE 1

Analyses of crosslinked butyl rubber before and after coating with epoxidized butyl rubber (AFM)

| Sample | Film Thickness (nm) | Film Roughness (nm) | Static CA (°) | Adv. CA (°) | Rec. CA (°) |
|---|---|---|---|---|---|
| Butyl rubber RB402 | 28 | 1.5 | 92 ± 1 | 103 ± 6 | 77 ± 17 |
| Epoxidized Butyl 2 | 43 | 4.7 | 88 ± 2 | 97 ± 6 | 72 ± 14 |
| Hydroxyl functionalized butyl 3 | 44.5 | 3.9 | 87.0 ± 0.4 | 99 ± 3 | 62 ± 19 |
| Acid functionalized butyl 4 | 41.3 | 8.2 | 86 ± 3 | 100 ± 6 | 76 ± 13 |

EXAMPLE 6

Epoxidized butyl 2 as a Compatibilizer

The wettability of the epoxidized butyl surfaces towards more hydrophilic polymers was investigated. A comparative study was performed where both regular butyl rubber or epoxidized butyl rubber were used as substrates to create thin films of various polymers. AFM imaging was qualitatively used to obtain the topography of the obtained thin films after spin-casting. To quantitatively evaluate the influence of the compatibilizer, contact angle measurements were performed following treatment of the films with HHIC. The hydrophilic polymers investigated in this example are polyvinylstearate (PVS), PMMA, and polycaprolactone (PCL).

Figures 5A, 5B:
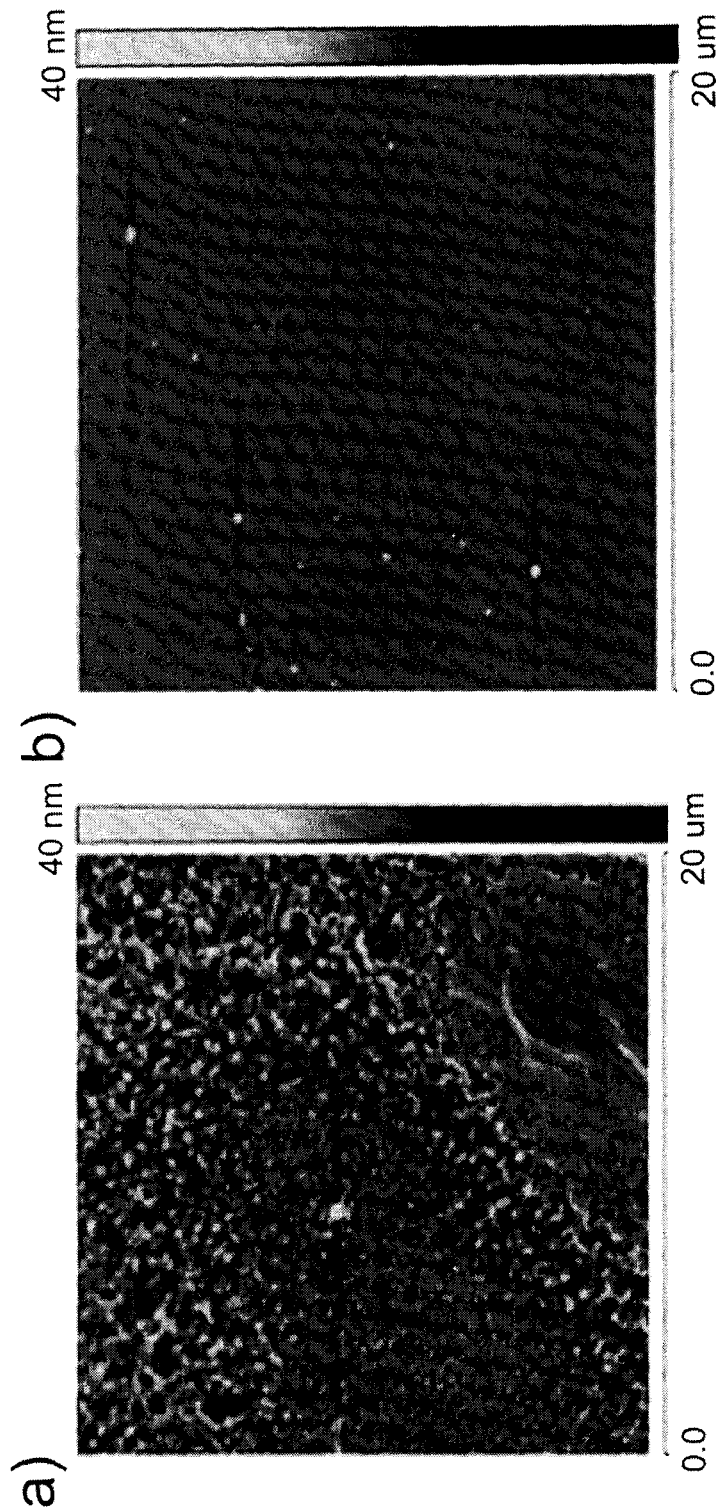
FIG. 5a shows AFM image (topography) of a film, having PVS spin cast onto butyl rubber; the image represents a 20×20 μm area.
FIG. 5b shows AFM image (topography) of a film, having PVS spin cast onto epoxidized butyl rubber; the image represents a 20×20 μm area.

As shown in FIG. 5, the coverage of the epoxidized butyl rubber surface was more homogeneous than the regular butyl rubber substrate. In addition, consistent with the AFM results (carried out using Method A), lower contact angles were obtained for the PVS coated epoxidized butyl rubber surfaces (Table 2).

TABLE 2

Contact Angle measurements of the PVS coated butyl rubber after HHIC treatment.

| | Concentration mg/mL | Static CA (°) | Adv. CA (°) | Rec. CA (°) |
|---|---|---|---|---|
| PVS on butyl | 2.5 | 94 ± 6 | 99 ± 3 | 77 ± 5 |
| | 5 | 100 ± 3 | 106 ± 2 | 89 ± 5 |
| PVS on epoxidized butyl | 2.5 | 85 ± 1 | 95 ± 3 | 76 ± 2 |
| | 5 | 80 ± 2 | 96 ± 2 | 64 ± 2 |

Figures 6A, 6B:
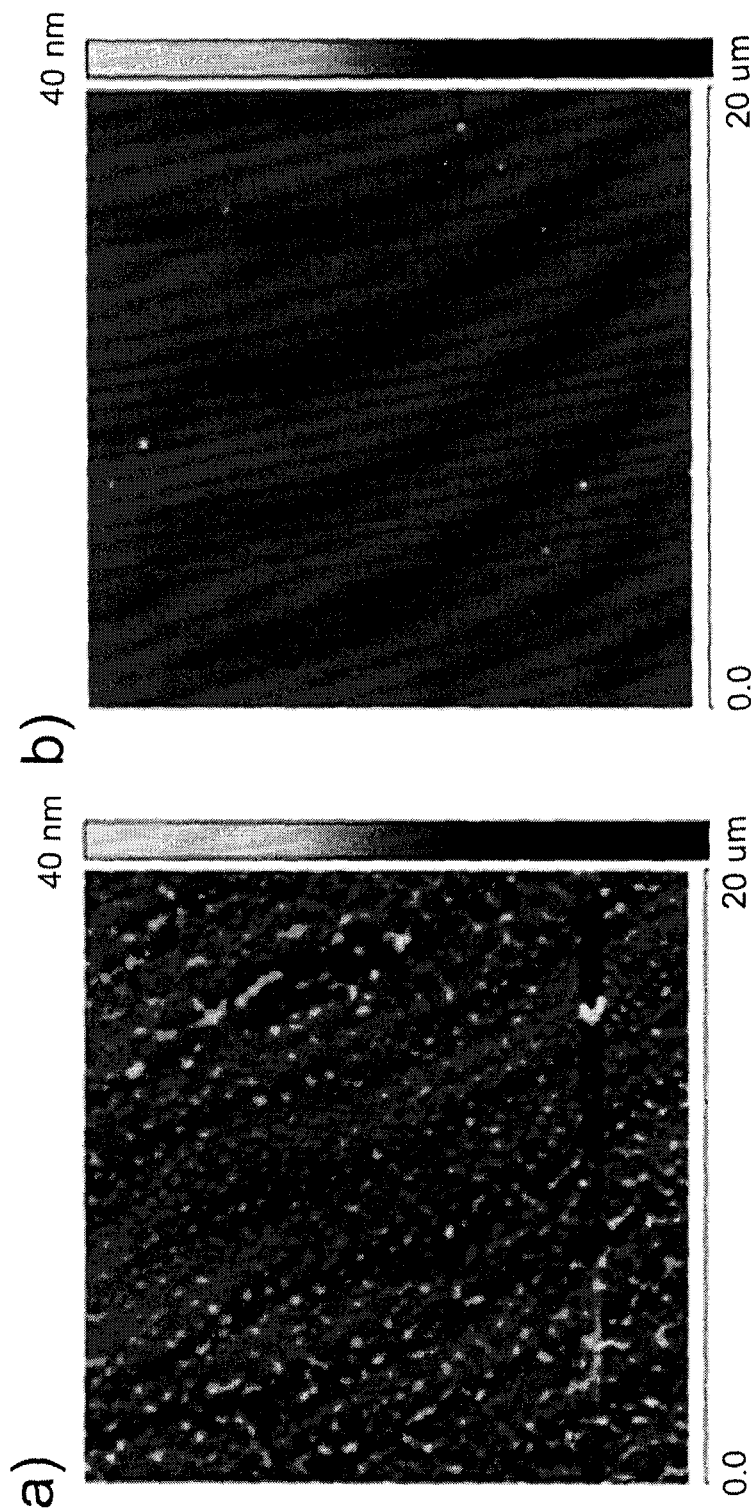
FIG. 6a shows AFM image (topography) of a film having PMMA spin cast onto butyl rubber.
FIG. 6b shows AFM image (topography) of a film having PMMA spin cast onto epoxidized butyl rubber.
Figures 7A, 7B:
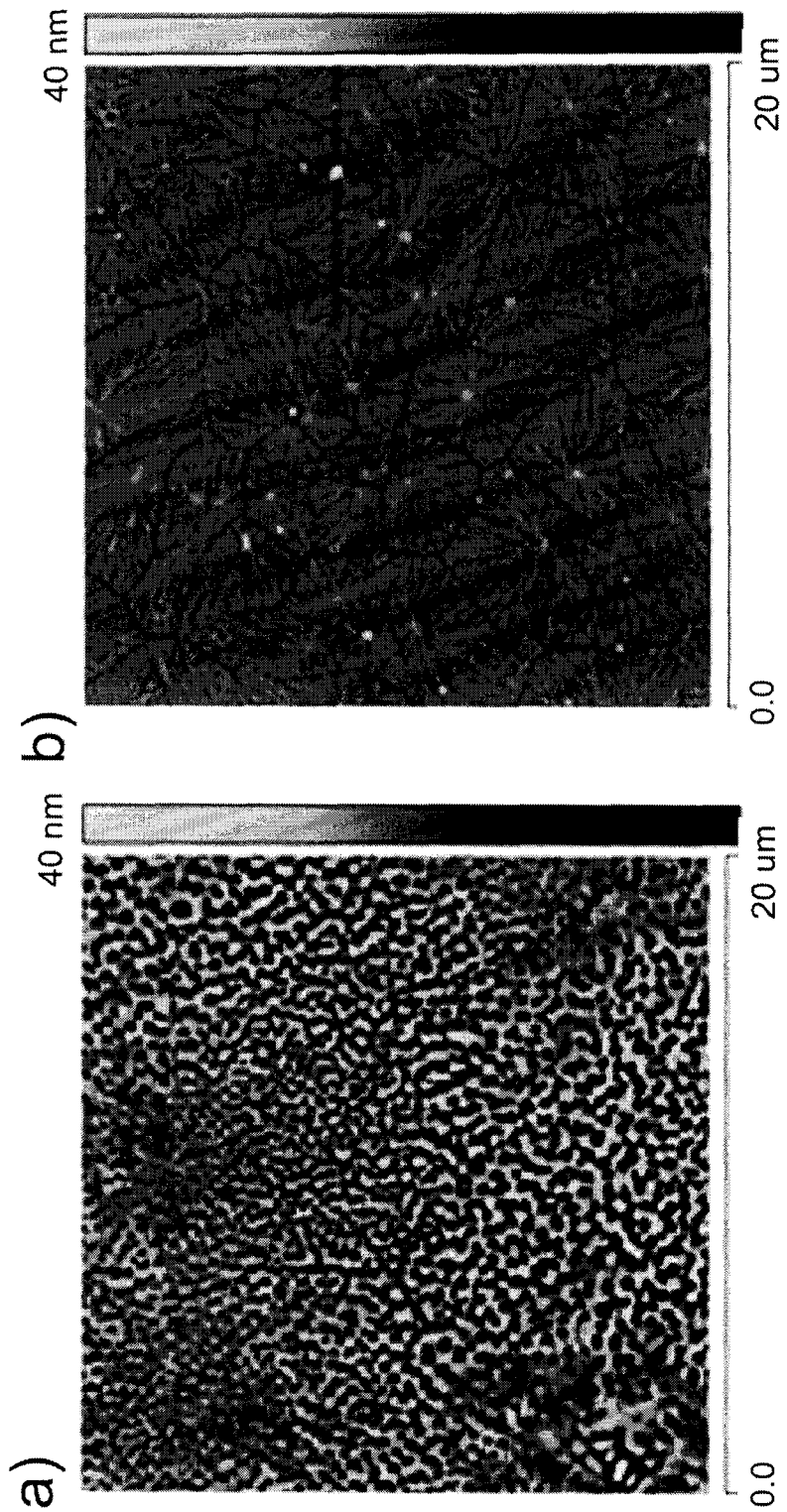
FIG. 7a shows AFM image (topography) of a film having PCL spin cast onto butyl rubber.
FIG. 7b shows AFM image (topography) of a film having PCL spin cast onto epoxidized butyl rubber.

The AFM results (carried out using Method B), also revealed a more homogeneous coating of the epoxidized butyl rubber surfaces with PMMA (FIG. 6) and PCL (FIG. 7). As shown in Tables 3 and 4, lower contact angles were also obtained for these surfaces.

TABLE 3

Contact Angle measurements of the PMMA coated butyl rubber after HHIC treatment.

| | Concentration mg/mL | Static CA (°) | Adv. CA (°) | Rec. CA (°) |
|---|---|---|---|---|
| PMMA on butyl | 2.5 | 89 ± 3 | 91 ± 2 | 55 ± 4 |
| | 5 | 82 ± 4 | 90 ± 1 | 44 ± 3 |
| PMMA on epoxidized butyl | 2.5 | 66 ± 5 | 85 ± 2 | 39 ± 2 |
| | 5 | 63 ± 1 | 74 ± 2 | 35 ± 1 |

TABLE 4

Contact Angle measurements of the PCL coated butyl rubber after HHIC treatment.

| | Concentration mg/mL | Static CA (°) | Adv. CA (°) | Rec. CA (°) |
|---|---|---|---|---|
| PCL on butyl | 2.5 | 80 ± 2 | 86 ± 2 | 57 ± 7 |
| | 5 | 76 ± 2 | 90 ± 3 | 58 ± 6 |
| PCL on epoxidized butyl | 2.5 | 65 ± 2 | 71 ± 3 | 44 ± 5 |
| | 5 | 64 ± 2 | 74 ± 2 | 46 ± 4 |

EXAMPLE 7

Figures 8A, 8B, 8C, 8D:
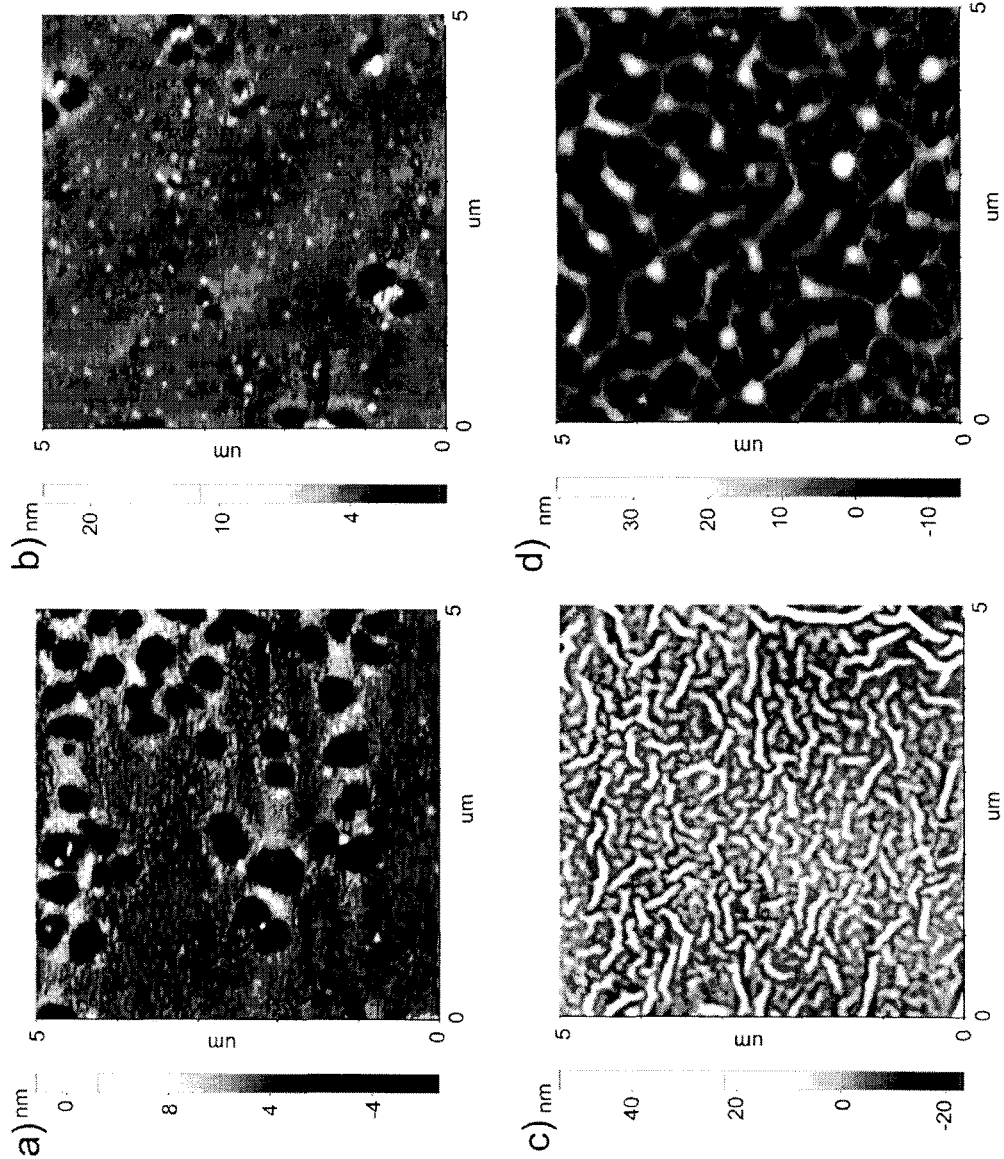
FIG. 8a shows AFM image (topography) of a film having PEO spin cast onto butyl rubber.
FIG. 8b shows AFM image (topography) of a film having PEO spin cast onto epoxidized butyl rubber 2.
FIG. 8c shows AFM image (topography) of a film having PEO spin cast onto hydroxyl functionalized butyl rubber 3.
FIG. 8d shows AFM image (topography) of a film having PEO spin cast onto acid functionalized butyl rubber 4.

Comparison of PEO Coated butyl Rubber Surface and Functionalized butyl Rubber Surfaces As described above for other hydrophilic polymers, the incompatibility between PEO and butyl rubber led to a film that was highly inhomogeneous with large drops of PEO observed on the surface of the hydrophobic elastomer (FIG. 8). The spin coating of PEO on the epoxidized butyl rubber surface created more homogeneous layers as indicated by AFM imaging (using Method B), and contact angle measurements (FIG. 8).

Similarly, PEO could also be coated onto butyl rubber using the hydroxyl and acid functionalized compatibilizers 3 and 4. The PEO was subsequently cross-linked by HHIC for 100 s to provide a stable film that resisted washing with water. Table 5 summarizes results from analyses of PEO coated surfaces.

TABLE 5

Analyses of PEO coatings

| Sample | Film Thickness (from AFM) (nm) | Film Roughness (from AFM) (nm) | Static CA (°) | Adv. CA (°) | Rec. CA (°) |
|---|---|---|---|---|---|
| PEO on Butyl RB402 (1) | 31.6 | 17.8 | 59 ± 1 | 43 ± 3 | 30 ± 11 |
| PEO on Epoxidized Butyl 2 | 55.8 | 7.1 | 49 ± 3 | 73 ± 8 | 33 ± 13 |
| PEO on Hydroxyl functionalized butyl 3 | 52.7 | 6.0 | 51 ± 3 | 58 ± 4 | 40 ± 9 |
| Acid functionalized butyl 4 on butyl RB402 | 52.8 | 11.3 | 48 ± 3 | 61 ± 4 | 37 ± 12 |

EXAMPLE 8

Resistance of PEO Coated Surfaces to Protein Adsorption

Experiments were conducted to verify that the resulting PEO coated surfaces could resist the adsorption of proteins. Fluorescence microscopy was selected as the primary technique to compare the protein adsorption to different surfaces (Model et al., *J. Biomed. Mater. Res.* 2000, 50, 90-96). Fibrinogen was selected as the protein of interest because it is a prevalent protein from plasma, involved in the clotting of blood. Fibrinogen has previously received considerable interest because it plays a pivotal role in the process of surface-induced thrombosis (Horbett, T. A. *Cardiovasc. Pathol.* 1993, 2, S137). A fluorescent fibrinogen adduct was prepared by its reaction with an activated rhodamine dye as previously reported (Bonduelle, C. V.; Gillies, E. R. *Macromolecules* 2010, 43, 9230-9233).

For comparison with the butyl rubber surfaces, a clean, hydrophilic silicon wafer was coated with PEO and treated by HHIC in the same manner as the PEO coated butyl surfaces. In addition, a coated silicon surface in which PEO was grafted chemically was prepared by the reaction of a silane functionalized PEO with clean glass according to the previously reported procedure (Jo, S.; Park, K. *Biomaterials* 2000, 21, 605-616). While the fluorescence method does not allow the actual masses of adsorbed protein to be determined, the inclusion of this chemically grafted control sample allows our results to be correlated and compared with a surface for which these values have been previously determined.

To measure the protein adsorption, the butyl, epoxidized butyl, PEO coated epoxidized butyl, PEO coated silicon wafer, and chemically grafted PEO surfaces were immersed in a 400 µg/mL solution of fluorescent fibrinogen for 2 hours. Following this, the surfaces were washed and confocal fluorescence microscopy was performed at 590 nm. The fluorescence was quantified for at least 10 random regions on each surface and at least 3 surfaces of each type were measured for statistical reasons.

Figure 9:
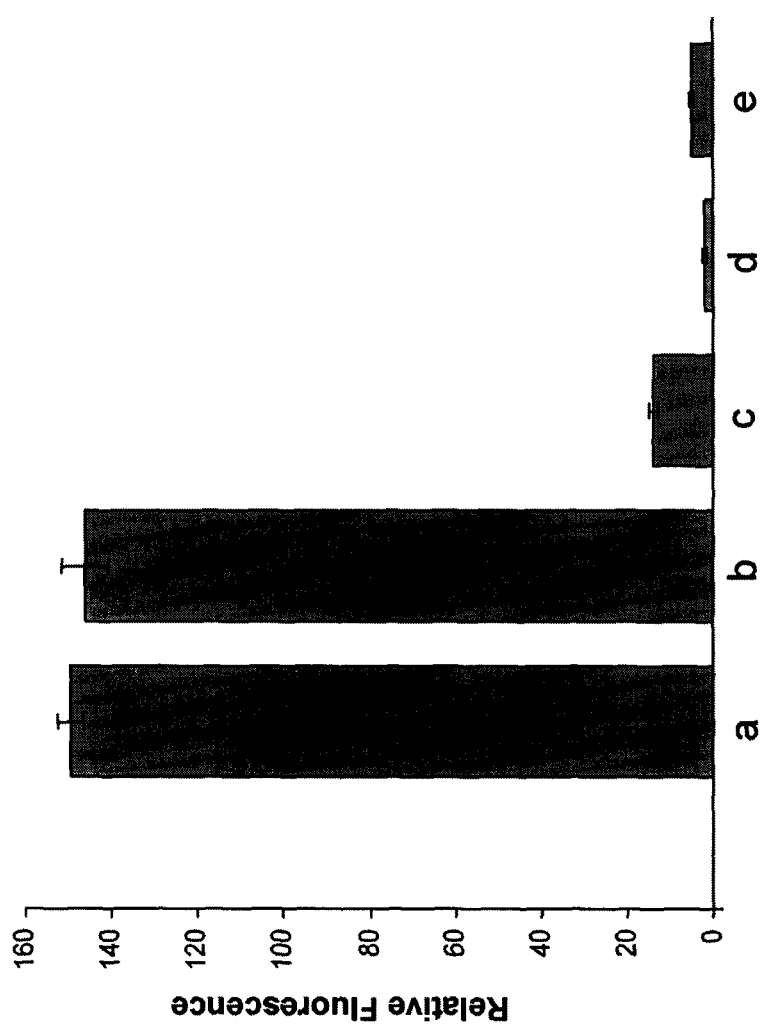
FIG. 9 shows relative fluorescence obtained by confocal microscopy corresponding to the adsorption of a fluorescently labeled fibrinogen on surfaces following HHIC: a) butyl RB 402, b) epoxidized butyl RB402, c) epoxidized butyl RB402 coated with PEO, d) PEO on clean silicon wafer, e) control surface of silane functionalized PEO grafted on glass (0.01 μg/cm$^2$), wherein error bars represent the standard deviation of 10 measurements on each of 3 samples.

As shown in FIG. 9, the butyl rubber and epoxidized butyl rubber surfaces exhibited intense fluorescence (using Method A) corresponding to high levels of protein adsorption, a result that can likely be attributed to their high hydrophobicities. In contrast, the PEO coated silicon wafer exhibited 80-fold lower fluorescence levels. The fluorescence levels of this surface compared favorably with those of the chemically grafted PEO surface. As this particular chemically grafted PEO surface has been measured to adsorb 0.01 µg/cm$^2$ of protein after 1 hour of immersion in a solution of 150 µg/mL, it can be inferred that the values for the cross-linked PEO coated silicon wafer would be in a similar range under the same experimental conditions. The PEO coated epoxidized butyl rubber exhibited approximately 10-fold less protein adsorption than on butyl or epoxidized butyl itself, demonstrating the efficacy of the compatibilizer layer in enabling the coating of butyl to provide surfaces that resist protein adsorption.

EXAMPLE 9

Resistance of the Surfaces to Cell Adhesion and Growth

Cell adhesion on a substrate is a necessary condition for survival and proliferation of the vast majority of mammalian cells in culture. As cells need to be attached to grow, the evaluation of cell growth on a surface can reflect the ability of this surface to resist cell adhesion. Therefore, the growth of cells on the surfaces was explored. Each surface was seeded with 10 000 $C_2C_{12}$ mouse myoblast cells per cm$^2$ and then the surfaces were incubated for 2 days in culture media. After fixation, the cell nuclei were stained with DAPI, and fluorescence confocal microscopy was used to count the number of cells on the surface. 10 random regions per surface were counted and the surfaces were evaluated in triplicate.

Figure 10:
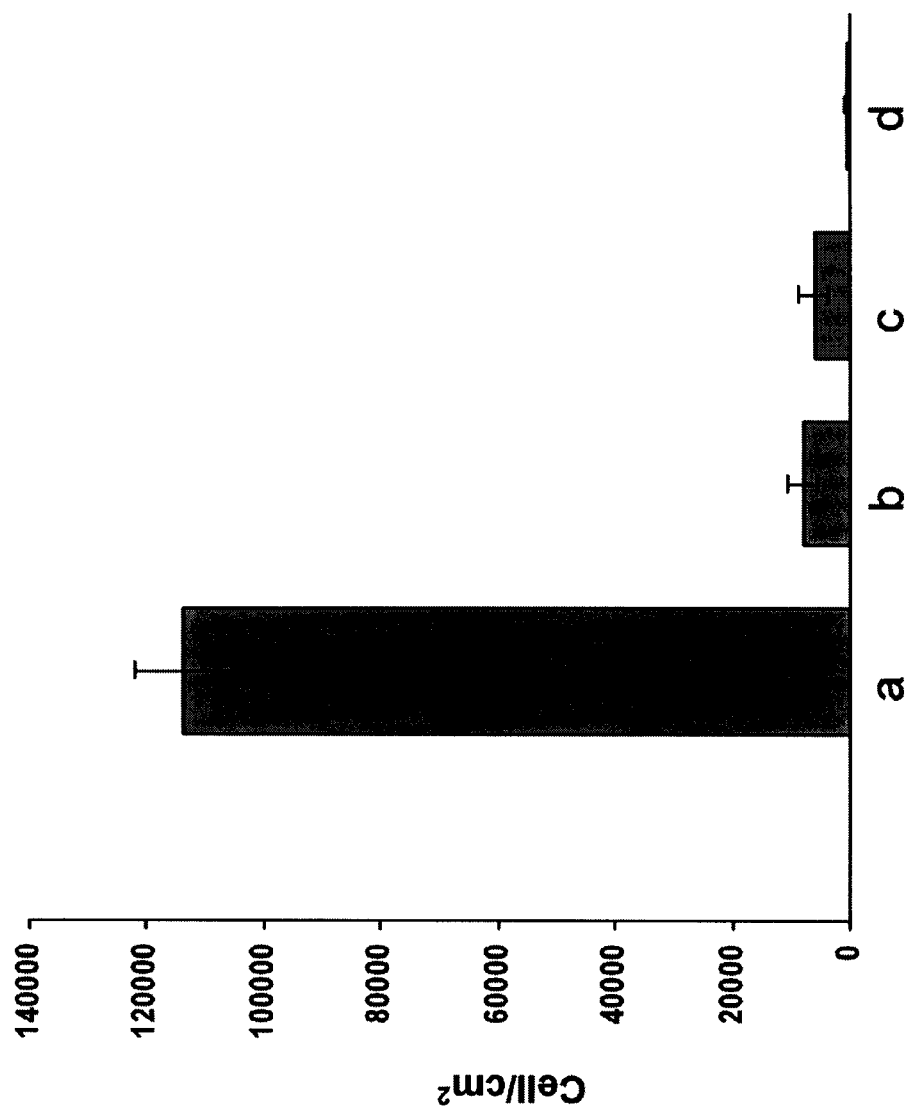
FIG. 10 shows show evaluation of cell growth on surfaces: a) bulk butyl rubber, b) butyl+epoxidized butyl+PEO after HHIC, c) control surface of silane functionalized PEO grafted on glass d) PEO coated silicon wafer following HHIC. Error bars represent the standard deviation of 10 measurements on each of 3 samples.

As shown in FIG. 10, it was found that bulk butyl rubber was a good substrate for cell growth, exhibiting similar cell growth to tissue culture polystyrene (approximately 200 000 cells/cm$^2$). In contrast, when butyl was coated first with epoxidized butyl as an compatibilizer layer, followed by PEO and HHIC, the number of cells decreased 10-fold, to a value similar to that observed for the control chemically grafted PEO surface. This reduction in cell adhesion and growth is likely tied to the resistance of these surfaces to protein adsorption as protein adsorption is thought to often be the first step in cell attachment to surfaces (Shard, A. G.; Tomlins, P. E. *Regenerative Med.* 2006, 1, 789-800).

All documents cited in the Detailed Description of the invention are, in relevant par, incorporated herein by reference; the citation of any document is not to be construed as an admission that it is prior art with respect to the present invention.

It is obvious that the foregoing embodiments of the invention are examples and can be varied in many ways. Such present or future variations are not to be regarded as a departure from the spirit and scope of the invention, and all such modifications as would be obvious to one skilled in the art are intended to be included within the scope of the following claims.

We claim:

1. A method of improving wettability of a substrate surface towards a hydrophilic polymer, the method comprising applying a compatibilizer to a substrate surface to increase wettability of the substrate surface towards a hydrophilic polymer, wherein the substrate is butyl rubber, and the compatibilizer comprises a functionalized copolymer comprising repeating units derived from at least one $C_4$-$C_8$ isoodefin and units derived from at least one $C_4$-$C_{16}$ conjugated diolefin, wherein one or more of the units derived from the at least one conjugate diolefin comprises an oxygen-containing functional group, derived by functionalizing a C—C double bond along a backbone of the copolymer with an oxygen containing functional group.

2. The method of claim 1, wherein the oxygen containing functional group is epoxide, hydroxyl, or —OC(O)—R, wherein R is H, $C_{1-6}$ alkyl, $C_{1-6}$ alkyl substituted with —O—$C_{1-6}$ alkyl, $C_{1-6}$ alkyl substituted with —C(O)R' or $C_{1-6}$ alkyl substituted with —O—$C_{1-6}$ alkyl-C(O)R', where R' is H, OH, $C_{1-6}$ alkyl or —O—$C_{1-6}$ alkyl.

3. The method of claim 1, wherein the functionalized copolymer comprises one or more functionalized isoprene units represented by the formula:

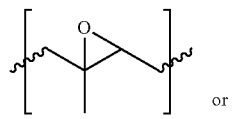

(I)

or

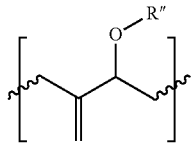

wherein R" is H or —C(O)—R, where R is H, $C_{1-6}$ alkyl, $C_{1-6}$ alkyl substituted with —O—$C_{1-6}$ alkyl, $C_{1-6}$ alkyl substituted with —C(O)R' or $C_{1-6}$ alkyl substituted with —O—$C_{1-6}$ alkyl-C(O)R', where R' is H, OH, $C_{1-6}$ alkyl or —O—$C_{1-6}$ alkyl.

4. The method of claim 1, wherein the butyl rubber is cured butyl rubber or crosslinked butyl rubber.

5. A method of improving wettability of a substrate surface towards a hydrophilic polymer, the method comprising applying a compatibilizer to a substrate surface to increase wettability of the substrate surface towards a hydrophilic polymer, wherein the substrate is a silicon material having a layer of hydrophobic polymer coated thereon, and the compatibilizer comprises a functionalized copolymer comprising repeating units derived from at least one $C_4$-$C_8$ isoolefin and units derived from at least one $C_4$-$C_{16}$ conjugated diolefin, wherein one or more of the units derived from the at least one conjugated diolefin comprises an oxygen-containing functional group, derived by functionalizing a C—C double bond along a backbone of the copolymer with an oxygen containing functional group.

6. The method of claim 5, wherein the hydrophobic polymer is a butyl rubber.

7. A method of coating a hydrophilic polymer on a non-hydrophilic substrate, the method comprising:
   a) applying a compatibilizer on a surface of the substrate to form an interfacial layer; wherein the compatibilizer comprises a functionalized copolymer comprising repeating units derived from at least one $C_4$-$C_8$ isoolefin and units derived from at least one $C_4$-$C_{16}$ conjugated diolefin, wherein one or more of the units derived from the at least one conjugated diolefin comprises an oxygen-containing functional group, derived by functionalizing a C—C double bond along a backbone of the copolymer with an oxygen containing functional group, and
   b) applying a hydrophilic polymer onto the interfacial layer obtained in step a).

8. The method of claim 7, wherein the compatibilizer is applied as a solution in a compatibilizer solubilizing solvent.

9. The method of claim 8, wherein the solvent is selected from the group consisting of hexane, chloroform, dichloromethane, acetone and tetrahydrofuran.

10. The method of claim 7, wherein the compatibilizer is applied via spin coating, dip coating or spray coating.

11. The method of claim 7, wherein the hydrophilic polymer is applied as a solution in a solvent which solubilizes the hydrophilic polymer.

12. The method of claim 11, wherein the solvent is selected from the group consisting of chloroform, dichloromethane, toluene, chlorobenzene, or tetrahydrofuran.

13. The method of claim 7, wherein the hydrophilic polymer is applied via spin coating, dip coating or spray coating.

14. The method of claim 7, further comprising crosslinking the interfacial layer onto the substrate.

15. The method of claim 7 or 14, further comprising crosslinking the hydrophilic polymer and the interfacial layer.

16. The method of claim 14, wherein the crosslinking is achieved by Hyperthermal Hydrogen induced Crosslinking (HHIC), crosslinking with activated species from Inert Gas-Casing, or electron beam crosslinking.

17. The method of claim 7, wherein the compatibilizer comprises from about 0.5 to about 20 mol % of repeating units derived from the conjugated diolefin and about 80 to 99.5 mol % of repeating units derived from the isoolefin.

18. The method of claim 7, wherein the isoolefin comprises isobutylene.

19. The method of claim 7, wherein the functionalized copolymer comprises one or more functionalized isoprene units represented by the formula:

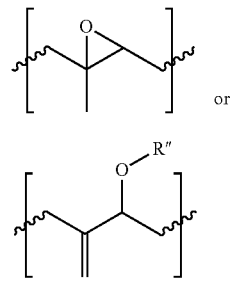

wherein R" is H or —C(O)—R, where R is H, $C_{1-6}$ alkyl, $C_{1-6}$ alkyl substituted with —O—$C_{1-6}$ alkyl, $C_{1-6}$ alkyl substituted with —C(O)R' or $C_{1-6}$ alkyl substituted with —O—$C_{1-6}$ alky-C(O)R', where R' is H, OH, $C_{1-6}$ alkyl or —O—$C_{1-6}$ alkyl.

20. The method of claim 7, wherein the substrate is silicon material or a hydrophobic polymer.

21. The method of claim 20, wherein the substrate is a cured film of butyl rubber or crosslinked film of butyl rubber.

22. The method of claim 7, wherein the substrate is a silicon material having a layer of hydrophobic polymer coated thereon.

23. The method of claim 20 or 22, wherein the hydrophobic polymer is butyl rubber.

24. The method of claim 7, wherein the hydrophilic polymer is poly(ethylene oxide) (PEO), poly(methyl methacrylate) (PMMA), a polyester, or polyvinylstearate (PVS).

* * * * *